US009764019B2

(12) United States Patent
Honda et al.

(10) Patent No.: US 9,764,019 B2
(45) Date of Patent: Sep. 19, 2017

(54) COMPOSITIONS CONTAINING COMBINATIONS OF BIOACTIVE MOLECULES DERIVED FROM MICROBIOTA FOR TREATMENT OF DISEASE

(71) Applicants: Vedanta Biosciences, Boston, MA (US); RIKEN, Wako-Shi, Saitama (JP)

(72) Inventors: Kenya Honda, Yokohama (JP); Bernat Olle, Cambridge, MA (US); Koji Atarashi, Yokohama (JP); Takeshi Tanoue, Yokohama (JP); Hiroshi Ohno, Yokohama (JP); Shinji Fukuda, Yokohama (JP); Koji Hase, Yokohama (JP)

(73) Assignees: Vedanta Biosciences, Inc., Cambridge, MA (US); RIKEN, Wako-shi, Saitama (JP)

( * ) Notice: Subject to any disclaimer, the term of this patent is extended or adjusted under 35 U.S.C. 154(b) by 0 days.

(21) Appl. No.: 14/903,377

(22) PCT Filed: Jul. 8, 2014

(86) PCT No.: PCT/US2014/045801
§ 371 (c)(1),
(2) Date: Jan. 7, 2016

(87) PCT Pub. No.: WO2015/006355
PCT Pub. Date: Jan. 15, 2015

(65) Prior Publication Data
US 2016/0144014 A1 May 26, 2016

Related U.S. Application Data

(60) Provisional application No. 61/844,204, filed on Jul. 9, 2013.

(51) Int. Cl.
*A61K 39/08* (2006.01)
*A61K 39/00* (2006.01)
*A61K 39/02* (2006.01)
*A61K 31/19* (2006.01)
*A61K 45/06* (2006.01)
*A61K 38/16* (2006.01)
*G01N 33/569* (2006.01)

(52) U.S. Cl.
CPC .............. *A61K 39/08* (2013.01); *A61K 31/19* (2013.01); *A61K 38/164* (2013.01); *A61K 39/0008* (2013.01); *A61K 45/06* (2013.01); *G01N 33/56977* (2013.01); *A61K 2039/577* (2013.01); *G01N 2333/70539* (2013.01); *G01N 2469/00* (2013.01)

(58) Field of Classification Search
CPC ...... A61K 35/741; A61K 39/00; A61K 39/02; A61K 39/08

USPC ............................ 424/184.1, 234.1, 2, 247.1
See application file for complete search history.

(56) References Cited

U.S. PATENT DOCUMENTS

| 4,576,936 A | 3/1986 | MacDonald |
| 6,368,586 B1 | 4/2002 | Jacob et al. |
| 2006/0240482 A1 | 10/2006 | Kwok et al. |
| 2012/0027734 A1 | 2/2012 | Van Immerseel et al. |

FOREIGN PATENT DOCUMENTS

| CA | 2850000 A1 | 4/2013 |
| FR | 2 383 662 A1 | 10/1978 |
| WO | WO 96/25380 A1 | 8/1996 |
| WO | WO 2007/009539 A2 | 1/2007 |

OTHER PUBLICATIONS

Genbank Submission; NIH/NCBI, Accession No. AY551005; Lodes et al.; May 5, 2014.
Genbank Submission; NIH/NCBI, Accession No. AY551006; Lodes et al.; May 5, 2014.
Allen et al., Mucus glycoprotein structure, gel formation and gastrointestinal mucus function. Ciba Found Symp. 1984;109:137-56.
Atarashi et al., Induction of colonic regulatory T cells by indigenous Clostridium species. Science. Jan. 21, 2011;331(6015):337-41. doi:10.1126/science.1198469. Epub Dec. 23, 2010.
Atarashi et al., $T_{reg}$ induction by a rationally selected mixture of Clostridia strains from the human microbiota. Nature. Aug. 8, 2013;500(7461):232-6. doi: 10.1038/nature12331. Epub Jul. 10, 2013.
Bäckhed et al., The gut microbiota as an environmental factor that regulates fat storage. Proc Natl Acad Sci U S A. Nov. 2, 2004;101(44):15718-23. Epub Oct. 25, 2004.
Hooper et al., Commensal host-bacterial relationships in the gut. Science. May 11, 2001;292(5519):1115-8.
Hooper et al., Molecular analysis of commensal host-microbial relationships in the intestine. Science. Feb. 2, 2001;291(5505):881-4.
Labat-Robert et al., Gastric mucus glycoproteins: Structure, functions and pathology. Pathologie Biologie. Dec. 1978;27(4):241-247.
Rakoff-Nahoum et al., Recognition of commensal microflora by toll-like receptors is required for intestinal homeostasis. Cell. Jul. 23, 2004;118(2):229-41.

(Continued)

*Primary Examiner* — Rodney P Swartz
(74) *Attorney, Agent, or Firm* — Wolf, Greenfield & Sacks, P.C.

(57) ABSTRACT

Compositions consisting of bioactive molecules derived from the microbiota of a mammal are provided herein. When administered orally with a colonic delivery system, the compositions are useful for the prophylaxis and treatment of diseases, in particular inflammatory, autoimmune and infectious diseases. The compositions comprise combinations of small molecules and bacterial antigens formulated in colonic delivery systems. Use of the compositions results in any or all of: induction of immune tolerance; strengthening of the gut mucosal barrier integrity; reduction of inflammation; and amelioration of a disease state caused by inflammation, an autoimmune reaction or an infectious agent.

8 Claims, 5 Drawing Sheets

(56) References Cited

OTHER PUBLICATIONS

Sealy et al., The effect of sodium butyrate on histone modification. Cell. May 1978;14(1):115-21.
Sonnenburg et al., Getting a grip on things: how do communities of bacterial symbionts become established in our intestine? Nat Immunol. Jun. 2004;5(6):569-73.
Spiro, Glycoproteins. Annu Rev Biochem. 1970;39:599-638.
Stappenbeck et al., Developmental regulation of intestinal angiogenesis by indigenous microbes via Paneth cells. Proc Natl Acad Sci U S A. Nov. 26, 2002;99(24):15451-5. Epub Nov. 13, 2002.

Figs. 4a-b

US 9,764,019 B2

SEQUENCE LISTING

<160> NUMBER OF SEQ ID NOS: 3

<210> SEQ ID NO 1
<211> LENGTH: 1482
<212> TYPE: DNA
<213> ORGANISM: Artificial Sequence
<220> FEATURE:
<223> OTHER INFORMATION: Synthetic Polynucleotide

<400> SEQUENCE: 1

```
atggtagtac agcacaattt acaggcaatg aactctaaca gaatgttagg catcacacag      60
aagacagcat ctaagtctac agaaaagtta tcttcaggtt acgcaatcaa ccgcgcagca     120
gacaacgcag caggtcttgc tatttctgag aagatgagaa agcagatcag aggacttaca     180
caggcttcta caaatgctga ggacggcatc agctctgtac agacagcaga aggcgctttg     240
acagaagtgc atgatatgct tcagagaatg aacgagctgg caattcaggc agcaaacggc     300
acaaactcag aagatgaccg ctcatacatt caggacgaaa ttgaccagct gacacaggaa     360
atcgatcgtg ttgctgagac aacaaagttc aatgagacat atctcttgaa gggtgacaca     420
aagaacgttg acgctatgga ctatacatat agctataagg cagttacaac gaatactgta     480
gcaagagctt cggttttagc agcagagaac acagctacag gtatgtcagt tagtatttca     540
tttgctgcaa acagcggcaa ggttactgca gctgactcta acaaccttgc aaaggctatc     600
agagatcagg gcttcacaat cacaacatct acccagaatg gtaaggttgt ttacggtctt     660
gagctgaacg gaagcgatgc aaaggcaaac tatacagttt caacagtaag tatggaagct     720
ggtacattca agatcctgaa ttctaataag caggttgttg catctgtaac aatatctaca     780
acagctagct ttaaaaaggt atctggtatg tcacagatcg ttacggcgta ctctgtatca     840
gcagcttatg cgacgggtga tgtatactct ctctatgacg cagacggaaa tgcaatttca     900
gcaaacaagc tggataagta ctttacggca ggcggcgcta cagaggcagg cggaatagct     960
actacacttt cagcaaactc tggtgtgcct aaggtttatg acgtactcgg aaaagaggtt    1020
tctgcagtaa gcattgcaag tactttagta acagcagtta aggataagac ggctgcattg    1080
aagatgaact tccatgtagg tgctgacgga acagataaca acaagattaa gatcaacatt    1140
gaggctatga cagctaagag tcttggagtt aacggtctga aggtgagcgg ttcgagcgga    1200
acaaacgcta caaacgctat cgagataatc gctggcgcta tcaagaaggt ttctacacag    1260
agatctgctc ttggtgcggt tcagaacaga ttagagcaca caatcaacaa cttggataac    1320
atcgttgaga acacaacagc agctgagtca ggaatccgcg atacagatat ggctacagag    1380
```

```
atggttaagt actctaacgc taatatcctt tcacaggcag gtcagtctat gcttgcacag    1440
tctaaccagt ctaaccaggg tgtacttcag ctcttacagt aa                       1482
```

<210> SEQ ID NO 2
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 2

```
Ser Ile Ile Asn Phe Glu Lys Leu
1               5
```

<210> SEQ ID NO 3
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 3

```
Ile Ser Gln Ala Val His Ala Ala His Ala Glu Ile Asn Glu Ala Gly
1               5                   10                  15

Arg
```

COMPOSITIONS CONTAINING COMBINATIONS OF BIOACTIVE MOLECULES DERIVED FROM MICROBIOTA FOR TREATMENT OF DISEASE

RELATED APPLICATIONS

This application is a national stage filing under 35 U.S.C. §371 of PCT International application PCT/US2014/045801, filed Jul. 8, 2014, which was published under PCT Article 21(2) in English, and claims the benefit under 35 U.S.C. §119(e) of U.S. provisional application Ser. No. 61/844,204, filed Jul. 9, 2013, the disclosures of which are incorporated by reference herein in their entireties.

FIELD

Described here are therapeutic combinations of molecules derived from the gut microbiota, more particularly therapeutic combinations of protein antigens and small molecules administered orally via colonic delivery systems.

BACKGROUND

Animals, including humans, host a multitude of microbes (collectively referred to as the host's microbiota) in anatomical locations including the mouth, esophagus, stomach, small intestine, large intestine, caecum, colon, rectum, vagina, skin, nasal cavities, ear, and lungs. The human microbiota is responsible for a multitude of critical processes, including development of the immune system, metabolism of carbohydrates, proteins, and xenobiotics formation and regeneration of the epithelium, fat storage, production of hormones, production of vitamins, and protection from pathogen infections, among others (Hooper L V, Gordon J I. Science. 2001;292:1115; Rakoff-Nahoum S, Paglino J, Eslami-Varzaneh F, Edberg S, Medzhitov R. Cell. 2004;118:229; Backhed F, et al. Proc. Natl. Acad. Sci. U.S.A. 2004;101:15718; Stappenbeck T S, Hooper L V, Gordon J I. Proc. Natl. Acad. Sci. U.S.A. 2002;99:15451;1 Sonnenburg J L, Angenent L T, Gordon J I. Nat. Immunol. 2004;5:569; Hooper L V, et al. Science. 2001; 291:881). Alterations of the human microbiota, which can be caused by a number of factors such as antibiotic use, excessive hygiene, diet, genetic background, or combinations of the above, have been associated with a number of infectious diseases (e.g., *C. difficile* infections), inflammatory, autoimmune, and allergic diseases (e.g., ulcerative colitis, Crohn's disease, Type 1diabetes, food allergies, asthma, rheumatoid arthritis), and metabolic diseases (e.g., Type 2 diabetes, metabolic syndrome, obesity, malnutrition), among others. These alterations can lead to a loss of tolerance against benign food antigens or benign commensal bacterial antigens, subsequent excessive inflammatory responses, metabolic dysregulation, and damage to the intestinal tissue, which compromises its ability to serve as a barrier between the gut lumen and the systemic circulation. Approaches for countering the harmful effects of microbiota alterations on health are limited, despite the key role that such alterations play in promoting human pathology. Interventions known to modulate the microbiota include antibiotics, prebiotics, probiotics and fecal transplants, each of which has limited effects and potential adverse effects. Additional approaches to countering the detrimental effects of microbiome alterations on human health which are efficacious are clearly needed, particularly compositions that can be manufactured with the quality standards of a pharmaceutical product.

SUMMARY

It is an object of the present disclosure to provide compositions that counter the detrimental effects of microbiome alterations on human health, are efficacious and can be manufactured with the quality standards of a pharmaceutical product. In particular, in order to develop drugs that induce tolerance to the microbiota, strengthen the gut barrier, and maintain or restore metabolic and immune homeostasis, it may be desirable to identify physiologically active substances produced by the microbiota that are responsible for its beneficial effects on the host and to devise methods to deliver these substances to the precise anatomical location where they can mediate such beneficial effects.

Compositions and methods of the present disclosure have been made in view of the above-described problems in the art. Certain microbiota-derived antigens and microbiota-derived small molecules, in combination, have synergistic effects on induction of tolerance, gut barrier integrity and reduction of inflammation, individually or in any combination thereof (e.g., on induction of tolerance and gut barrier integrity, on induction of tolerance and reduction of inflammation, on gut barrier integrity and reduction of inflammation, or on induction of tolerance, gut barrier integrity and reduction of inflammation. Described herein are compositions that (1) comprise (a) one or more short-chain fatty acid or one or more short-chain fatty acid derivative, (b) a (at least one, one or more) GPR109 ligand, (c) a (at least one, one or more) GPR43 ligand, (d) a (at least one, one or more) histone-deacetylase (HDAC) inhibitor, (e) one or more antigen derived from one or more bacteria belonging to *Clostridium* Cluster IV, or *Clostridium* Cluster XIVa, or *Clostridium* Cluster XVIII, or one or more antigen derived from bacteria from any combination of *Clostridium* Cluster IV, *Clostridium* Cluster XIVa, and *Clostridium* Cluster XVIII (e.g., one or more antigen derived from bacteria from *Clostridium* Cluster IV and one or more antigen derived from bacteria from *Clostridium* Cluster XIVa, one or more antigen derived from bacteria from *Clostridium* Cluster IV and one or more antigen derived from *Clostridium* Cluster XVIII, one or more antigen derived from bacteria from *Clostridium* Cluster XIVa and one or more antigen derived from bacteria from *Clostridium* Cluster XVIII, one or more antigen derived from bacteria from *Clostridium* Cluster IV, or one or more antigen derived from bacteria from *Clostridium* Cluster XIVa and one or more antigen derived from bacteria from *Clostridium* Cluster XVIII), or (f) a (at least one, one or more) flagellin polypeptide, or that comprise (g) a combination of at least one of (a)-(d) and at least one of (e)-(f); and (2) induce tolerance (e.g., induce proliferation and/or accumulation of regulatory T cells (Tregs)), strengthen gut barrier integrity, reduce inflammation, or any combination thereof. For example, a composition may (1) comprise a combination of (a) and (e), (a) and (f), (b) and (e), (b) and (f), (c) and (e), (c) and (f), (d) and (e) or (d) and (f); and (2) only induce tolerance, only strengthen gut barrier integrity, only reduce inflammation, induce tolerance and strengthen gut barrier integrity, induce tolerance and reduce inflammation, strengthen gut barrier integrity and reduce inflammation, or induce tolerance, strengthen gut barrier integrity and reduce inflammation.

In some embodiments, the combination of (g) include any combination of: one of the following: (a) one or more short-chain fatty acid or one or more short-chain fatty acid derivative; or (b) a (at least one, one or more) GPR109 ligand; or (c) a (at least one, one or more) GPR43 ligand; or (d) a (at least one, one or more) histone-deacetylase (HDAC) inhibitor, and either: (e) one or more antigen derived from one or more bacteria belonging to *Clostridium* Cluster IV, or *Clostridium* Cluster XIVa, or *Clostridium* Cluster XVIII or one or more antigen derived from bacteria from any combination of *Clostridium* Cluster IV, *Clostridium* Cluster XIVa, and *Clostridium* Cluster XVIII (e.g., one or more antigen derived from bacteria from *Clostridium* Cluster IV and one or more antigen derived from bacteria from *Clostridium* Cluster XIVa; one or more antigen derived from bacteria from *Clostridium* Cluster IV and one or more antigen derived from *Clostridium* Cluster XVIII; one or more antigen derived from bacteria from *Clostridium* Cluster XIVa and one or more antigen derived from bacteria from *Clostridium* Cluster XVIII; one or more antigen derived from bacteria from *Clostridium* Cluster IV, one or more antigen derived from bacteria from *Clostridium* Cluster XIVa and one or more antigen derived from bacteria from *Clostridium* Cluster XVIII) or (f) a (at least one, one or more) flagellin polypeptide.

Described herein are compositions that (1) comprise (a) one or more short-chain fatty acid or short-chain fatty acid derivative; (b) a (at least one or more) GPR109 ligand; (c) a (at least one or more) GPR43 ligand; (d) a (at least one or more) histone-deacetylase (HDAC) inhibitor; (e) one or more antigen derived from one or more bacteria belonging to *Clostridium* Cluster IV, or *Clostridium* Cluster XIVa, or *Clostridium* Cluster XVIII; (f) a flagellin polypeptide; or (g) a combination of at least one of (a)-(d) and one of (e)-(f), and (2) induce tolerance (e.g., induce proliferation and/or accumulation of regulatory T cells (Tregs), strengthen gut barrier integrity, and reduce inflammation. The present invention pertains to therapeutic combinations of molecules derived from the gut microbiota, more particularly to combinations of protein antigens and small molecules administered orally via colonic delivery systems.

In one embodiment, the short-chain fatty acid or short-chain fatty acid derivative is a substance selected from the group consisting of: butyrate, isobutyrate, propionate, acetate, tributyrin, pivaloyloxymethyl butyrate, and monoacetone glucose 3-butyrate. In one embodiment, the GPR109 ligand is a substance selected from the group consisting of: pyridine-3-carboxylic acid (also known as niacin or Vitamin B3), a niacin derivative, 4,5-Dihydro-5-methyl-4-oxo-5-phenyl-2-furancarboxylic acid, 5-carboxy-2-methyl-1-oxidopyrazin-1-ium, GSK-256073, GSK256073, ARI-3037MO, INCB019602, INCB19602, MK-0354, MK-0354, a barbituric acid derivative, an anthranilic acid derivative, a pyrazole derivative, an isoxazole derivative, a xanthine derivative, a cycloalkane derivative, a pyrazolopyrimidine, and a thyophene. In one embodiment, the GPR43 ligand is a substance selected from the group consisting of: acetate, formate, phenylacetamide 1 [(S)-2-(4-chlorophenyl)-3-methyl-N-(thiazol-2-yl)butanamide], phenylacetamide 2 [(S)-2-(4-chlorophenyl)-N-(5-fluorothiazol-2-yl)-3-methylbutanamide], propionate, and valerate. In another aspect, the HDAC inhibitor is a substance selected from the group consisting of: trichostatin A, (N-(2-aminophenyl)-N'-phenyl-octanediamide), 2-(4-butoxyphenyl)-N-hydroxyacetamide, MS-275, suberoylanilide hydroxamic acid, and RG 2833. In some embodiments, the one or more antigen derived from bacteria belonging to *Clostridium* Cluster IV, or *Clostridium* Cluster XIVa, or *Clostridium* Cluster XVIII is a substance selected from the group consisting of: one or more heat treated inactivated bacteria belonging to *Clostridium* Cluster IV, or *Clostridium* Cluster XIVa, or *Clostridium* Cluster XVIII, a purified membrane fraction from one or more bacteria belonging to *Clostridium* Cluster IV, or *Clostridium* Cluster XIVa, or *Clostridium* Cluster XVIII, flagellin, a flagellin-like sequence, a flagellin component protein, CBir1, Fla-X, FliC, FliD, FlgK, FlgC, and FlgE.

In one embodiment, the compositions contain a mixture of short-chain fatty acids including sodium acetate, sodium propionate, sodium butyrate, sodium isobutyrate or any combination of two, three, four (or more) of short-chain fatty acids including, but not limited to, sodium acetate, sodium propionate, sodium butyrate, and sodium isobutyrate, which can optimally promote the production of active-form TGF-β, a cytokine which regulates inflammation via induction of Tregs and controls the permeability of the gut barrier.

The composition described herein is administered orally to an individual in need thereof, such as a patient in need thereof. The composition may be administered in a number of oral forms that preferentially deliver the active agents to colonic tissue, including pH-sensitive formulations (e.g., formulations coated with enteric polymers that release drug when the pH becomes more alkaline after passage through the stomach); formulations that delay the release of the drug for a lag time of 3-5 hours, roughly equivalent to small intestinal transit time, thereby securing delivery to the colon; formulations containing bioadhesive polymers that selectively provide adhesion to the colonic mucosa; and formulations containing molecules that target receptors preferentially expressed in dendritic cells, intestinal epithelial cells, and macrophages.

In one aspect, administration of a composition described herein causes induction of Tregs that are transcription factor Foxp3-positive Tregs or IL-10-producing Tregs. Assessment of the extent of induction of proliferation or accumulation of Tregs that results from administration of a composition described herein can be carried out by a variety of approaches, such as by measurement of the number of Foxp3-expressing Tregs in a patient sample (such as a biopsy or blood sample), promotion of IL-10 expression, promotion of CTLA4 expression, promotion of IDO expression, or suppression of IL-4 expression.

Immunity in an individual can be suppressed through administration of the subject composition, such as through administration of a pharmaceutical composition or through ingestion of the composition in a food or beverage or as a dietary supplement. The subject composition can be used, for example, to prevent or treat autoimmune disease, allergic diseases, inflammatory diseases, to suppress the immunological rejection of a transplanted organ, or to treat cancer.

Also provided herein are methods of inducing tolerance, strengthening the gut barrier, and/or reducing inflammation in an individual in need thereof. The method comprises administering to an individual a composition described herein. In some embodiments, the composition comprises (a) one or more short-chain fatty acid or short-chain fatty acid derivative; (b) a GPR109 ligand; (c) a GPR43 ligand; (d) a histone-deacetylase inhibitor; (e) one or more antigen derived from bacteria belonging to *Clostridium* Clusters IV, XIVa, and XVIII; (f) a flagellin polypeptide; or (g) a combination of at least one of (a)-(d) and one of (e)-(f), and is administered to an individual in need of prevention, reduction or treatment of a condition or disease.

Also provided is a method for detecting and quantifying induction of tolerance in a subject. The method quantifies, in a sample from a subject, the frequency of Tregs that recognize antigens expressed by bacteria belonging to *Clostridium* Cluster IV, or bacteria belonging to *Clostridium* Cluster XIVa, or bacteria belonging to *Clostridium* Cluster XVIII. In some embodiments, the antigen that is recognized by Tregs is flagellin. Complexes comprising four MHC Class II tetramers with streptavidin, a molecule having tetrameric binding sites for biotin to which a fluorochrome is bound, are prepared. The MHC Class II chains are obtained by recombinant expression of polynucleotides encoding a desired epitope, for example an epitope present in an antigen expressed by bacteria belonging to *Clostridium* Cluster IV, or *Clostridium* Cluster XIVa, or *Clostridium* Cluster XVIII.

DETAILED DESCRIPTION

I. Definitions

Figure 1:
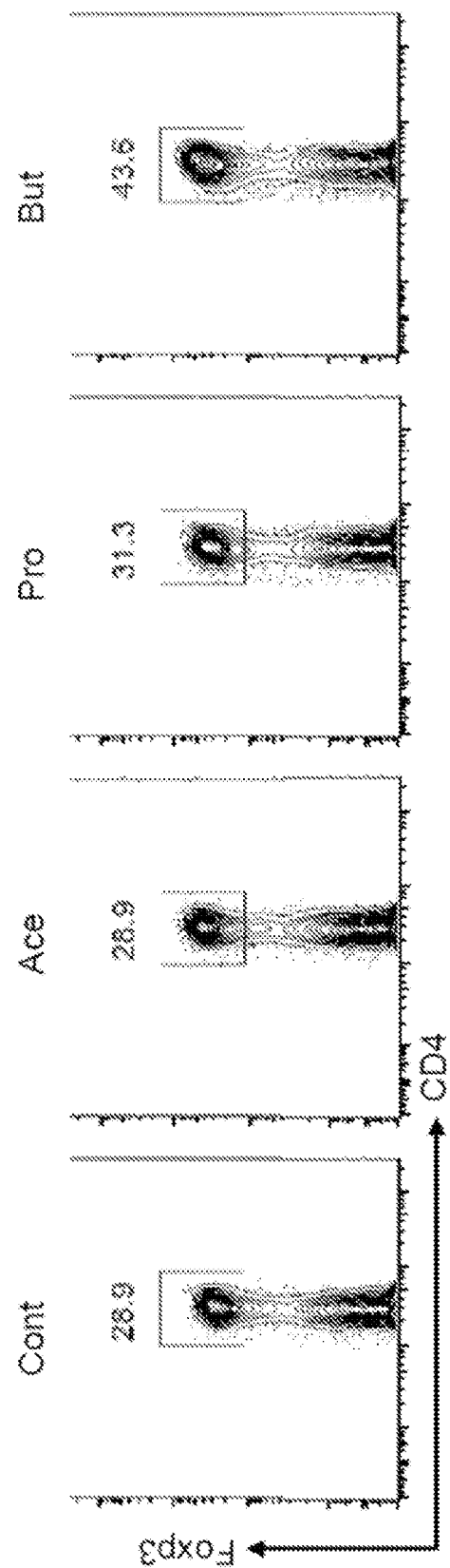
FIG. 1 shows representative FACS plots showing that butyrate (But) induces the accumulation of Tregs cells in vitro.

The term "microbiota" refers, collectively, to the entirety of microbes found in association with a higher organism, such as a human.

The term "commensal" refers to organisms that are normally harmless to a host, and can also establish mutualistic relations with said host.

The term "human microbiome" refers to the totality of microbes, their genetic elements (genomes), and environmental interactions in the human body The terms "tolerance" and "immune tolerance" refer to the process by which the immune system does not attack an antigen.

The terms "tolerance induction" or "inducing tolerance" refer to a process by which tolerance to external antigens can be created by manipulating the immune system.

The term "regulatory T cells" or "Tregs" refers to T cells that suppress an abnormal or excessive immune response and play a role in immune tolerance. The regulatory T cells are typically transcription factor Foxp3-positive CD4-positive T cells. The regulatory T cells of the present invention also include transcription factor Foxp3-negative regulatory T cells that are IL-10-producing CD4-positive T cells.

The term "induces proliferation or accumulation of regulatory T cells" refers to an effect of inducing the differentiation of immature T cells into regulatory T cells, which differentiation leads to the proliferation and/or the accumulation of regulatory T cells. Further, the meaning of "induces proliferation or accumulation of regulatory T cells" includes in-vivo effects, in vitro effects, and ex vivo effects.

The term "strengthening gut barrier integrity" refers to a process of improving the ability of the epithelial barrier of the gastrointestinal tract to act as a barrier between the "outside" lumen and host tissues by reducing its permeability or leakiness. Several defects related to intestinal barrier function have been found in patients with autoimmune and inflammatory diseases. For example, a "leaky gut" is a primary defect in inflammatory bowel disease (IBD) pathogenesis; substances that damage the barrier, such as NSAIDs, may cause flares in IBD patients, and defects in the gut barrier are sufficient to trigger chronic gut inflammation.

II. Compositions Having Effect of Inducing Tolerance, Strengthening Gut Barrier Integrity, and Reducing Inflammation The authors have discovered that bacteria belonging to *Clostridium* Cluster IV, or *Clostridium* Cluster XIVa, or *Clostridium* Cluster XVIII, previously shown to have the ability of inducing colonic regulatory T cells and preventing the development of IBD in animals (Atarashi et al., Science, 331(6015):337-41, 2011), produce two types of secretions that, together, synergize to induce tolerance, strengthen barrier function, and reduce inflammation. The two types of secretions are short-chain fatty acids, particularly butyrate, and protein antigens, particularly flagellin polypeptides.

Described herein are compositions that induce tolerance (e.g., induce proliferation and/or accumulation of regulatory T cells (Tregs), strengthen gut barrier integrity, and reduce inflammation. In some embodiments, the compositions comprise, as active ingredient(s), (a) one or more short-chain fatty acid or short-chain fatty acid derivative; (b) a (at least one or more) GPR109 ligand; (c) a (at least one or more) GPR43 ligand; (d) a (at least one or more) histone-deacetylase (HDAC) inhibitor; (e) one or more antigen derived from bacteria belonging to *Clostridium* Cluster IV, or *Clostridium* Cluster XIVa, or *Clostridium* Cluster XVIII; (f) a flagellin polypeptide; or (g) a combination of at least one of (a)-(d) and one of (e)-(f).

In one embodiment, the short-chain fatty acid is a substance selected from the group consisting of: butyrate, isobutyrate, propionate, and acetate. Such molecules are naturally produced in large amounts by bacteria belonging to *Clostridium* Cluster IV, or *Clostridium* Cluster IVa, or *Clostridium* Cluster VIII in the human colon. In a preferred embodiment, the short-chain fatty acid substance is butyrate. Synthetic derivatives of butyrate with similar properties as their natural counterpart such as tributyrin, pivaloyloxymethyl butyrate, and monoacetone glucose 3-butyrate can also be used to that effect.

A composition containing a mixture of sodium acetate, sodium propionate, sodium butyrate, and sodium isobutyrate, can optimally promote the production of active-form TGF-β in culture supernatants of epithelial cell lines. In turn, an environment rich in active-form TGF-β helps expansion and differentiation of Tregs, reduces inflammation, and strengthens the gut barrier integrity.

In one embodiment, substances that bind to GPR109A can be used as a component of the compositions described herein. GPR109A is a G-protein-coupled receptor expressed in the lumen-facing apical membrane of colonic and intestinal epithelial cells that recognizes butyrate with low affinity, as previously shown in the art. Typical concentrations of butyrate in colonic lumen (millimolar) are sufficient to activate the receptor maximally. GPR109A-binding substances used as components of the compositions described herein can be selected from the group consisting of: pyridine-3-carboxylic acid (also known as niacin or Vitamin B3), a niacin derivative, 4,5-Dihydro-5-methyl-4-oxo-5-phenyl-2-furancarboxylic acid, 5-carboxy-2-methyl-1-oxidopyrazin-1-ium, GSK-256073, GSK256073, ARI-3037MO, INCB019602, INCB19602, MK-0354, MK-0354, a barbituric acid derivative, an anthranilic acid derivative, a pyrazole derivative, an isoxazole derivative, a xanthine derivative, a cycloalkane derivative, a pyrazolopyrimidine, and a thyophene.

In one embodiment, substances that bind to GPR43 can be used as a component of the compositions described herein. GPR43 is a G-protein-coupled receptor that recognizes acetate and propionate. GPR43-binding substances used as components of the compositions described herein can be selected from the group consisting of: acetate, formate, phenylacetamide 1 [(S)-2-(4-chlorophenyl)-3-methyl-N-(thiazol-2-yl)butanamide], phenylacetamide 2 [(S)-2-(4-chlorophenyl)-N-(5-fluorothiazol-2-yl)-3-methylbutanamide], propionate, and valerate.

In one embodiment, substances that inhibit a histone deacetylase (HDAC) can be used as a component of the compositions described herein. Treatment of naïve T cells with butyrate enhances histone H3 acetylation in the Foxp3 gene locus and butyrate thus regulates differentiation of Treg cells by mediating epigenetic modifications. HDAC inhibiting substances used as components of the compositions described herein can be selected from the group consisting of: trichostatin A, (N-(2-aminophenyl)-N'-phenyl-octanediamide), 2-(4-butoxyphenyl)-N-hydroxyacetamide, MS-275, suberoylanilide hydroxamic acid, and RG 2833.

Production of short-chain fatty acids alone does not fully account for the ability of bacteria belonging to *Clostridium* Cluster IV, or *Clostridium* Cluster IVa, or *Clostridium* Cluster VIII to induce tolerance, strengthen barrier function, and reduce inflammation. Antigens expressed by bacteria belonging to *Clostridium* Cluster IV, or *Clostridium* Cluster IVa, or or *Clostridium* Cluster VIII also contribute to induce tolerance, strengthen barrier function, and reduce inflammation. In some embodiments, the compositions described herein contain one or more bacterial antigen selected from the group consisting of: one or more heat treated inactivated bacteria belonging to *Clostridium* Cluster IV, or *Clostridium* Cluster XIVa, or *Clostridium* Cluster XVIII or any combination of bacteria belonging to *Clostridium* Cluster IV, or *Clostridium* Cluster XIVa, or *Clostridium* Cluster XVIII; a purified membrane fraction from one or more bacteria belonging to *Clostridium* Cluster IV, or *Clostridium* Cluster XIVa, or *Clostridium* Cluster XVIII or any combination of bacteria belonging to *Clostridium* Cluster IV, or *Clostridium* Cluster XIVa, or *Clostridium* Cluster XVIII, flagellin, a flagellin-like sequence, a flagellin component protein, CBir1, Fla-X, FliC, FliD, FlgK, FlgC, and FlgE. Purified membrane fractions refer to bacterial membranes that have been at least partially purified from other components of a bacterial cell. Purified membrane fractions from bacteria belonging *Clostridium* Cluster IV, or *Clostridium* Cluster XIVa, or *Clostridium* Cluster XVIII can be obtained by using methods known in the art such as mechanical grinding of bacterial cells followed by ultracentrifugation and followed by extraction with trifluoroethanol and chloroform. In a preferred embodiment, a purified membrane fraction is obtained from one or more bacteria belonging to *Clostridium* Cluster IV, or *Clostridium* Cluster XIVa, or *Clostridium* Cluster XVIII any combination of bacteria belonging to *Clostridium* Cluster IV, or *Clostridium* Cluster XIVa, or *Clostridium* Cluster XVIII, selected from *Clostridium saccharogumia*, *Clostridium ramosum* JCM1298, *Clostridium ramosum*, *Flavonifractor plautii*, *Pseudoflavonifractor capillosus* ATCC 29799, *Clostridium hathewayi*, *Clostridium saccharolyticum* WM1, *Bacteroides* sp. MANG, *Clostridium saccharolyticum*, *Clostridium scindens*, *Lachnospiraceae bacterium* 5_1_57FAA, *Lachnospiraceae bacterium* 6_1_63FAA, *Clostridium* sp. 14616, *Clostridium bolteae* ATCC BAA-613, cf. *Clostridium* sp. MLG055, *Erysipelotrichaceae bacterium* 2_2_44A, *Clostridium indolis*, *Anaerostipes caccae*, *Clostridium bolteae*, *Lachnospiraceae bacterium* DJF_VP30, *Lachnospiraceae bacterium* 3_1_57FAA_CT1, *Anaerotruncus colihominis*, *Anaerotruncus colihominis* DSM 17241, *Ruminococcus* sp. ID8, *Lachnospiraceae bacterium* 2_1_46FAA, *Clostridium lavalense*, *Clostridium asparagiforme* DSM 15981, *Clostridium symbiosum*, *Clostridium symbiosum* WAL-14163, *Eubacterium contortum*, *Clostridium* sp. D5, *Oscillospiraceae bacterium* NML 061048, *Oscillibacter valericigenes*, *Lachnospiraceae bacterium* A4, *Clostridium* sp. 316002/08, and *Clostridiales bacterium* 1_7_47FAA, *Blautia cocoides*, and *Anaerostipes caccae* DSM 14662. Flagellin proteins are abundantly produced by bacteria belonging to *Clostridium* Clusters IV, XIVa, and XVIII. Flagellin, flagellin-like sequences, flagellin component proteins, and flagellin polypeptides can be manufactured using methods known in the art including, for example, production in bacterial recombinant hosts or liquid-phase or solid-phase peptide synthesis.

The composition may be administered in the form of a pharmaceutical composition, a dietary supplement, or a food or beverage (which may also be an animal feed), or may be used as a reagent for an animal model experiment. The composition can be used suitably as a composition having an immunosuppressive effect. The immunosuppressive effect can be evaluated, for example, as follows. Regulatory T cells isolated from an experimental animal, such as a mouse, to which the composition of the present invention is orally administered are caused to act on effector T-cells (CD4+ CD25– cells) isolated from the spleen, and the proliferation ability thereof is measured by using the intake amount of [3H]-thymidine as an index.

Specific examples of target diseases for which the composition is useful for treatment (reducing adverse effects or prevention) include autoimmune diseases, allergic diseases, infectious diseases, and rejection in organ transplantations, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondy loarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn *purpurea*, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, yersinia and salmonella associated arthropathy, spondyloarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondy litis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulindependent diabetes mellitus, sympathetic ophthalmia, pulmonary hypertension secondary to connective tissue disease, Goodpasture's syndrome, pulmonary manifestation of polyarteritis nodosa, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis, and diarrhea.

Additional examples of target diseases for which the composition is useful for treatment include colon cancer, cystic fibrosis, celiac disease, Type 2 diabetes, and autism-related immunopathologies. These diseases are characterized by a reduction of bacteria belonging to *Clostridium* Clusters IV and XIV, or a reduction of bacteria belonging to *Clostridium* Cluster IV or *Clostridium* Cluster XIV, in the gastrointestinal microbiota.

Compositions described herein can also be used as a pharmaceutical composition for preventing or treating infectious diseases in an individual whose resistance to the infectious diseases is impaired, for example because of damage due to excessive inflammation caused by the immunity or due to an alteration of the patient's microbiome. Examples of infectious pathogens that impair maintenance or recovery of homeostasis of a host, and which eventually bring about such immunopathological tissue damage include Salmonella, Shigella, *Clostridium difficile*, Mycobacterium (which cause the disease tuberculosis), protozoa (which cause malaria), filarial nematodes (which cause the disease filariasis), Schistosoma (which cause schistosomiasis), Toxoplasma (which cause the disease toxoplasmosis), Leishmania (which cause the disease leishmaniasis), HCV and HBV (which cause the disease hepatitis C and hepatitis B), and herpes simplex viruses (which cause the disease herpes).

The amount of the composition to be administered or ingested can be determined empirically, taking into consideration such factors as the age, body weight, gender, symptoms, health conditions, of an individual who will receive it, as well as the kind of composition (a pharmaceutical product, a food or beverage) to be administered or ingested. For example, the amount per administration or ingestion is generally 0.01 mg/kg body weight to 100 mg/kg body weight, and, in specific embodiments, 1 mg/kg body weight to 10 mg/kg body weight. The composition may be administered to an individual once, or it may be administered more than once. If the composition is administered more than once, it can be administered on a regular basis (for example, once a day, once every two days, once a week, once every two weeks, once a month, once every 6 months, or once a year) or on an as needed or irregular basis. The appropriate frequency of administration (which may depend on host genetics, age, gender, and health or disease status of the subject, among other factors) may be determined empirically.

III. Delivery Systems

The combined effects of *Clostridium*-derived short-chain fatty acids and *Clostridium*-derived antigens on induction of tolerance, gut barrier integrity, and reduction of inflammation are strongly dependent on physical proximity of these substances to the gut barrier. In a physiological context, these substances are typically secreted by bacteria that live in close proximity to the colonic intestinal wall. If the *Clostridium*-derived short-chain fatty acids and *Clostridium*-derived antigens are administered orally to a subject without being formulated in a colonic delivery system, they have limited or inadequate efficacy because the *Clostridium*-derived antigens are degraded by proteases during passage in the gastrointestinal tract and the short-chain fatty acids are rapidly absorbed in the small intestine before reaching the colon. Formulating the compositions described herein in delivery systems that preferentially target their release to colonic tissue greatly enhances the ability of the compositions to induce tolerance, increase gut barrier integrity, and reduce of inflammation.

General Strategies to Enable Delivery to the Colon

Numerous methods have been described in the art to enable general delivery of drugs to the colon, and any of them can be combined with the novel features of this invention to improve delivery to a niche in the colon. Such methods include pH-sensitive formulations (e.g., formulations coated with enteric polymers that release drug when the pH move towards a more alkaline range, after passage through the stomach); formulations that delay the release of the drug for a lag time of 3-5 hours, roughly equivalent to small intestinal transit time, thereby securing delivery to the colon; drugs coated with bioadhesive polymers that selectively provide adhesion to the colonic mucosa (e.g., see U.S. Pat. No. 6,368,586); delivery systems that incorporate protease inhibitors to prevent proteolytic activity in the gastrointestinal tract from degrading biologic drug agents; and formulations containing molecules that target receptors preferentially expressed in dendritic cells, such as CD205 Dendritic-Cell Specific Intercellular Adhesion Molecule 3-Grabbing Nonintegrin (DC-SIGN) and Langerin, receptors preferentially expressed in intestinal epithelial cells, and receptors preferentially expressed in macrophages such as anionic lipids, muramyl tripeptide (MTP), Arg-Gly-Asp (RGD), Anti-VCAM-1, Anti-CC52, Anti-CC531, Anti-CD11c/DEC-205, lectins (such as Mann-C4-Chol, Man2DOG, aminophenyl-alfa-D-mannopyranoside, Man3-DPPE), bovine serum albumin derivatives, O-steroly amylopectin, fibronectin, and galactosyl.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions. "Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995) which provides information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, $6^{th}$ Ed. (Media, Pa.: Williams & Wilkins, 1995).

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

Delayed release formulations are created by coating a solid dosage form with a film of a polymer which is insoluble in the acid environment of the stomach, and soluble in the neutral environment of small intestines. The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit®. L30D-55 and L100-55 (soluble at pH 5.5 and above), Eudragit®. L-100 (soluble at pH 6.0 and above), Eudragit®. S (soluble at pH 7.0 and above, as a result of a higher degree of esterification), and Eudragits®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The particles can be prepared entirely from a therapeutic agent, or from a combination of the agent and a surfactant. The particles can be made of a variety of materials. Both inorganic and organic materials can be used. For example, ceramics may be used. Polymeric and non-polymeric materials, such as fatty acids, may be used to form aerodynamically light particles. Other suitable materials include, but are not limited to, gelatin, polyethylene glycol, trehalose, and dextran. Particles with degradation and release times ranging from seconds to months can be designed and fabricated, based on factors such as the particle material.

In addition to a therapeutic or diagnostic agent (or possibly other desired molecules for delivery), the particles can include excipients such as a sugar, such as lactose, a protein, such as albumin, and/or a surfactant.

Enteric Coated Capsules: "Gastric resistant natural polymer," as used herein, refers to natural polymers or mixtures of natural polymers which are insoluble in the acidic pH of the stomach. "Film-forming natural polymer," as used herein, refers to polymers useful for surface coatings that are applied by spraying, brushing, or various industrial processes, which undergo film formation. In most film-formation processes, a liquid coating of relatively low viscosity is applied to a solid substrate and is cured to a solid, high-molecular-weight, polymer-based adherent film possessing the properties desired by the user. For most common applications, this film has a thickness ranging from 0.5 to 500 micrometers (0.0005 to 0.5 millimeters, or 0.00002 to 0.02 inches).

"Gelling agent," as used herein, refers to substances that undergo a high degree of cross-linking or association when hydrated and dispersed in the dispersing medium, or when dissolved in the dispersing medium. This cross-linking or association of the dispersed phase alters the viscosity of the dispersing medium. The movement of the dispersing medium is restricted by the dispersed phase, and the viscosity is increased.

Gastric resistant film-forming compositions containing (1) a gastric resistant natural polymer; (2) a film-forming natural polymer; and optionally (3) a gelling agent, are described herein. Exemplary gastric resistant natural polymers include, but are not limited to, pectin and pectin-like polymers which typically consist mainly of galacturonic acid and galacturonic acid methyl ester units forming linear polysaccharide chains. Typically these polysaccharides are rich in galacturonic acid, rhamnose, arabinose and galactose, for example the polygalacturonans, rhamnogalacturonans and some arabinans, galactans and arabinogalactans. These are normally classified according to the degree of esterification. In high (methyl) ester ("HM") pectin, a relatively high portion of the carboxyl groups occur as methyl esters, and the remaining carboxylic acid groups are in the form of the free acid or as its ammonium, potassium, calcium or sodium salt. Useful properties may vary with the degree of esterification and with the degree of polymerization. Pectin, in which less than 50% of the carboxyl acid units occur as the methyl ester, is normally referred to as low (methyl) ester or LM-pectin. In general, low ester pectin is obtained from high ester pectin by treatment at mild acidic or alkaline conditions. Amidated pectin is obtained from high ester pectin when ammonia is used in the alkaline deesterification process. In this type of pectin some of the remaining carboxylic acid groups have been transformed into the acid amide. The useful properties of amidated pectin may vary with the proportion of ester and amide units and with the degree of polymerization. In one embodiment, the gastric resistant natural polymer is pectin. The gastric resistant natural polymer is present in an amount less than about 5% by weight of the composition, preferably from about 2 to about 4% by weight of the composition.

Exemplary film-forming natural polymers include, but are not limited to, gelatin and gelatin-like polymers. In a preferred embodiment, the film-forming natural polymer is gelatin. A number of other gelatin-like polymers are available commercially. The film-forming natural polymer is present in an amount from about 20 to about 40% by weight of the composition, preferably from about 25 to about 40% by weight of the composition.

The compositions can optionally contain a gelling agent. Exemplary gelling agents include divalent cations such as $Ca^{2+}$ and $Mg^{2+}$. Sources of these ions include inorganic calcium and magnesium salts and calcium gelatin. The gelling agent is present in an amount less than about 2% by weight of the composition, preferably less than about 1% by weight of the composition.

One or more plasticizers can be added to the composition to facilitate the film-forming process. Suitable plasticizers include glycerin, sorbitol, sorbitans, maltitol, glycerol, polyethylene glycol, polyalcohols with 3 to 6 carbon atoms, citric acid, citric acid esters, triethyl citrate and combinations thereof. The concentration of the one or more plasticizers is from about 8% to about 30% by weight of the composition. In one embodiment, the plasticizer is glycerin and/or sorbitol.

The film-forming composition can be used to prepare soft or hard shell gelatin capsules which can encapsulate a liquid or semi-solid fill material or a solid tablet (Softlet®) containing an active agent and one or more pharmaceutically acceptable excipients. Alternatively, the composition can be administered as a liquid with an active agent dissolved or dispersed in the composition.

The film-forming composition can be used to prepare soft or hard capsules using techniques well known in the art. For example, soft capsules are typically produced using a rotary die encapsulation process. Fill formulations are fed into the encapsulation machine by gravity.

The capsule shell can contain one or more plasticizers selected from the group consisting of glycerin, sorbitol, sorbitans, maltitol, glycerol, polyethylene glycol, polyalcohols with 3 to 6 carbon atoms, citric acid, citric acid esters, triethyl citrate and combinations thereof.

In addition to the plasticizer(s), the capsule shell can include other suitable shell additives such as opacifiers, colorants, humectants, preservatives, flavorings, and buffering salts and acids.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

Soft or hard capsules can be used to deliver a wide variety of pharmaceutically active agents. Suitable agents include small molecules, proteins, nucleic acid, carbohydrates, lipids, and full organisms.

Fill formulations may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to surfactants, humectants, plasticizers, crystallization inhibitors, wetting agents, bulk filling agents, solubilizers, bioavailability enhancers, pH adjusting agents, and combinations thereof.

Alternatively, the composition can be administered as a liquid with an active agent dissolved (e.g. solution) or dispersed (e.g., suspension) in the composition. Suitable active agents are described above. The solution or suspension may be prepared using one or more pharmaceutically acceptable excipients. Suitable excipients include, but are not limited to, surfactants, humectants, plasticizers, crystallization inhibitors, wetting agents, bulk filling agents, solubilizers, bioavailability enhancers, pH adjusting agents, flavorants and combinations thereof Mucoadhesive Particles and methods of manufacturing: In general terms, adhesion of polymers to tissues may be achieved by (i) physical or mechanical bonds, (ii) primary or covalent chemical bonds, and/or (iii) secondary chemical bonds (e.g., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (e.g., Van der Waals interactions) and stronger specific interactions, which include hydrogen bonds. The hydrophilic functional groups responsible for forming hydrogen bonds are the hydroxyl (—OH) and the carboxylic groups (—COOH).

Adhesive polymeric microspheres have been selected on the basis of the physical and chemical bonds formed as a function of chemical composition and physical characteristics, such as surface area, as described in detail below. These microspheres are characterized by adhesive forces to mucosa of greater than 11 mN/cm$^2$. The size of these microspheres range from between a nanoparticle to a millimeter in diameter. The adhesive force is a function of polymer composition, biological substrate, particle morphology, particle geometry (e.g., diameter) and surface modification.

Classes of Polymers Useful in Forming Bioadhesive Microspheres: Suitable polymers that can be used to form bioadhesive microspheres include soluble and insoluble, biodegradable and nonbiodegradable polymers. These can be hydrogels or thermoplastics, homopolymers, copolymers or blends, natural or synthetic. A key feature, however, is that the polymer must produce a bioadhesive interaction between 110 N/m2 (11 mN/cm2) and 100,000 N/m2 when applied to the mucosal surface of rat intestine.

In order for bioadhesive particles to embed themselves or become engulfed in the mucus lining the GI tract, the radius of the individual particles should be as thick as the thickness of the natural mucous layer. It has been shown that the gastric mucous layer thickness typically varies from 5 to 200μ in the rat and 10 to 400μ in man. Occasionally, however, it can reach thicknesses as great as 1000μ in man, as described by Spiro, R. G., "Glycoproteins," Annual Review of Biochemistry, 39, 599-638, 1970; Labat-Robert, J. & Decaeus, C., "Glycoproteins du Mucus Gastrique: Structure, Fonction, et Pathologie," Pathologie et Biologie (Paris), 24, 241, 1979; Allen, A., Hutton, D. A., Pearson, J. P., & Sellers, L. A., "Mucus Glycoprotein Structure, Gel Formation and Gastrointestinal Mucus Function" in Mucus and Mucosa, Ciba Foundation Symposium 109 (eds. J. Nugent & M. O'Connor), pp. 137 (London: Pitman, 1984). In the past, two classes of polymers have appeared to show useful bioadhesive properties: hydrophilic polymers and hydrogels. In the large class of hydrophilic polymers, those containing carboxylic groups (e.g., poly[acrylic acid]) exhibit the best bioadhesive properties. One could infer that polymers with the highest concentrations of carboxylic groups should be the materials of choice for bioadhesion on soft tissues. In other studies, the most promising polymers were: sodium alginate, carboxymethylcellulose, hydroxymethylcellulose and methylcellulose. Some of these materials are water-soluble, while others are hydrogels.

Rapidly bioerodible polymers such as poly[lactide-co-glycolide], polyanhydrides, and polyorthoesters, whose carboxylic groups are exposed on the external surface as their smooth surface erodes, are excellent candidates for bioadhesive drug delivery systems. In addition, polymers containing labile bonds, such as polyanhydrides and polyesters, are well known for their hydrolytic reactivity. Their hydrolytic degradation rates can generally be altered by simple changes in the polymer backbone.

Representative natural polymers include proteins, such as zein, modified zein, casein, gelatin, gluten, serum albumin, or collagen, and polysaccharides, such as cellulose, dextrans, polyhyaluronic acid, polymers of acrylic and methacrylic esters and alginic acid. Representative synthetic polymers include polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Synthetically modified natural polymers include alkyl celluloses, hydroxyalkyl celluloses, cellulose ethers, cellulose esters, and nitrocelluloses. Other polymers of interest include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate)polyethylene, polypropylene, poly(ethylene glycol), poly(ethylene oxide), poly(ethylene terephthalate), poly(vinyl acetate), polyvinyl chloride, polystyrene, polyvinyl pyrrolidone, and polyvinylphenol. Representative bioerodible polymers include polylactides, polyglycolides and copolymers thereof, poly(ethylene terephthalate), poly(butic acid), poly(valeric acid), poly(lactide-co-caprolactone), poly [lactide-co-glycolide], polyanhydrides, polyorthoesters, blends and copolymers thereof.

IV. Engineered Bacteria Expressing a *Clostridium* Antigen and Short-Chain Fatty Acids Described herein are engineered organisms that express at least one *Clostridium*-derived antigen and at least one short-chain fatty acid. In a preferred embodiment, the *Clostridium*-derived antigen is flagellin and the short-chain fatty acid is butyrate. The organism may be a genetically engineered bacteria or a genetically engineered yeast. Preferably, the organism is a genetically engineered bacteria, such as a bacteria belonging to the genus *Clostridium*, a lactic acid bacteria, or *E. coli*. In a preferred embodiment, said organism is a Gram positive organism belonging to *Clostridium* Clusters IV or XIVa. Said organism is able to express at least on antigen and at least one short-chain fatty acid in vivo in the colonic mucosa of an animal. For example, PCR fragments containing the coding regions of flagellin (e.g., GenBank accession numbers AY551005 or AY551006) and of enzymes involved in the synthesis of butyrate such as Acetyl-CoA C-acetyltransferase, 3-hydroxybutyryl CoA dehydrogenase, enoyl-CoA hydratase, butyryl-CoA dehydrogenase, phosphate butyryltransferase, and butyrate kinase can be cloned into an organism, and recombinant vectors comprising these PCR clones can be constructed. The recombinant antigens and short-chain fatty acids produced by these engineered bacteria can induce tolerance, increase gut barrier integrity, and reduce inflammation in a subject in need thereof. The present specification also relates to pharmaceutical compositions comprising engineered organisms expressing at least one *Clostridium*-derived antigen and one short-chain fatty acid as described above.

V. Methods of Treatment

As described above, and as shown in Examples, administration of the compositions to an individual makes it possible to induce tolerance, strengthen gut barrier integrity, and reduce inflammation in the individual. This provides a method of inducing tolerance, strengthening the gut barrier, and reducing inflammation in an individual in need thereof. The method comprises administering to an individual a composition described herein. In some embodiments, the composition comprises (a) one or more short-chain fatty acid or short-chain fatty acid derivative; (b) a (at least one or more) GPR109 ligand; (c) a (at least one or more) GPR43 ligand; (d) a (at least one or more) histone-deacetylase inhibitor; (e) one or more antigen derived from bacteria belonging to *Clostridium* Clusters IV, XIVa, or XVIII; (f) a flagellin polypeptide; or (g) a combination of at least one of (a)-(d) and one of (e)-(f) is administered to an individual in need of prevention, reduction or treatment of a condition or disease. The composition is administered (provided) to the individual in sufficient quantity to produce the desired effect of inducing tolerance, strengthening the gut barrier, and reducing inflammation. It may be administered to an individual in need of treatment, reduction in the severity of or prevention of at least one disease selected from an autoimmune disease, an inflammatory disease, an allergic disease, or an infectious disease.

Whether administration of the composition induces tolerance can be determined by using, as an index, increase or reinforcement of at least one of the following: the number of regulatory T cells, the ratio of regulatory T cells in the T cell group of the colon, a function of regulatory T cells, or expression of a marker of regulatory T cells. A specific approach is measurement counts or percentage of Foxp3-expressing Tregs in a patient sample, such as a biopsy or a blood sample, promotion (enhancement) of IL-10 expression, promotion (enhancement) of CTLA4 expression, promotion (enhancement) of IDO expression, or suppression of IL-4 expression as the index of the induction of proliferation or accumulation of regulatory T cells. Whether administration of the composition strengthens barrier function can be determined by using, as an index, increase in production of active form TGF-β and/or tight junction-related proteins by intestinal epithelial cells. Whether administration of the composition reduces inflammation can be determined by using, as an index, increase in production of anti-inflammatory cytokines such as IL-10 and/or TGF-β, or decrease in production of pro-inflammatory cytokines such as IL-4.

Methods for detecting such expression include northern blotting, RT-PCR, and dot blotting for detection of gene expression at the transcription level; ELISA, radioimmunoassays, immunoblotting, immunoprecipitation, and flow cytometry for detection of gene expression at the translation level. Samples that may be used for measuring such an index include tissues and fluids obtained from an individual, such as blood, a biopsy, or a fecal sample.

VI. Methods for Detecting and Quantifying Induction of Tolerance in a Subject

Described herein are also immunoassays to detect and measure activation of T cells, particularly specific Treg subsets that recognize antigens expressed by bacteria belonging to *Clostridium* Clusters IV, XIVa, and XVIII. Such immunoassays can be used to determine and quantify whether administration of the composition induces tolerance in a subject. In some embodiments, the immunoassay quantifies the frequency of Tregs that recognize a flagellin epitope in the context of presentation by MHC Class II molecules. Complexes of four MHC Class II tetramers with streptavidin, a molecule having tetrameric binding sites for biotin, to which a fluorochrome is bound, are prepared. The MHC Class II chains are obtained by recombinant expression of polynucleotides encoding a desired epitope, for example a flagellin epitope, in host cells. Populations of Tregs specific for a *Clostridium* antigen, such as Tregs specific for a flagellin epitope, in samples from a subject, are readily detected even when present in very low numbers by use of this method. For example, a sample obtained from a subject such as a sample of peripheral blood lymphocytes (PBLs) containing a diverse population of T cells, can be contacted with the tetramer reagents described herein. When contacted with the diverse population of T cells in the sample, the tetramers containing epitopes recognized by a T cell in the sample bind to the matched T cell. The contents of the reaction can be analyzed using flow cytometry, to quantify those T cells having an MHC tetramer bound thereto.

EXAMPLES

Following are examples, which describe specific aspects. They are not intended to be limiting in any way.

Example 1

First, to gain mechanistic insight into the induction of Tregs by bacteria belonging to *Clostridium* Clusters IV, XIVa, and XVIII, germ-free mice were colonized with a cocktail of bacteria comprising bacterial strains belonging to *Clostridium* Cluster IV, bacterial strains belonging to *Clostridium* Cluster XIVa, and bacterial strains belonging to *Clostridium* Cluster XVIII ("*Clostridium*-colonized mice"). To identify metabolites potentially involved in Treg induction, the hundreds of metabolites present in the luminal composition of *Clostridium*-colonized, ex-germ free mice were painstakingly investigated with NMR-based metabolome analysis coupled with principal component analysis (PCA). This resulted in identification of short-chain fatty acids including acetate, propionate, isobutyrate, and particularly butyrate, as responsible for Treg induction. The influence of acetate, propionate, and butyrate on Treg induction in vitro was measured as follows: Splenic naïve (CD44$^{lo}$CD62L$^{hi}$) CD4+ T cells were stimulated with anti-CD3 and anti-CD28 mAb-coated beads and cultured in the presence of T-cell antigen receptor signaling and TGF-β with or without each of these short-chain fatty acids listed above. Supplementation of each short chain fatty acid, but in particular butyrate, enhanced differentiation of Treg cells compared to a no treatment control (FIG. 1). These observations illustrate that short chain fatty acids, and in particular butyrate, play an important role in inducing Tregs.

Example 2

Figure 2:
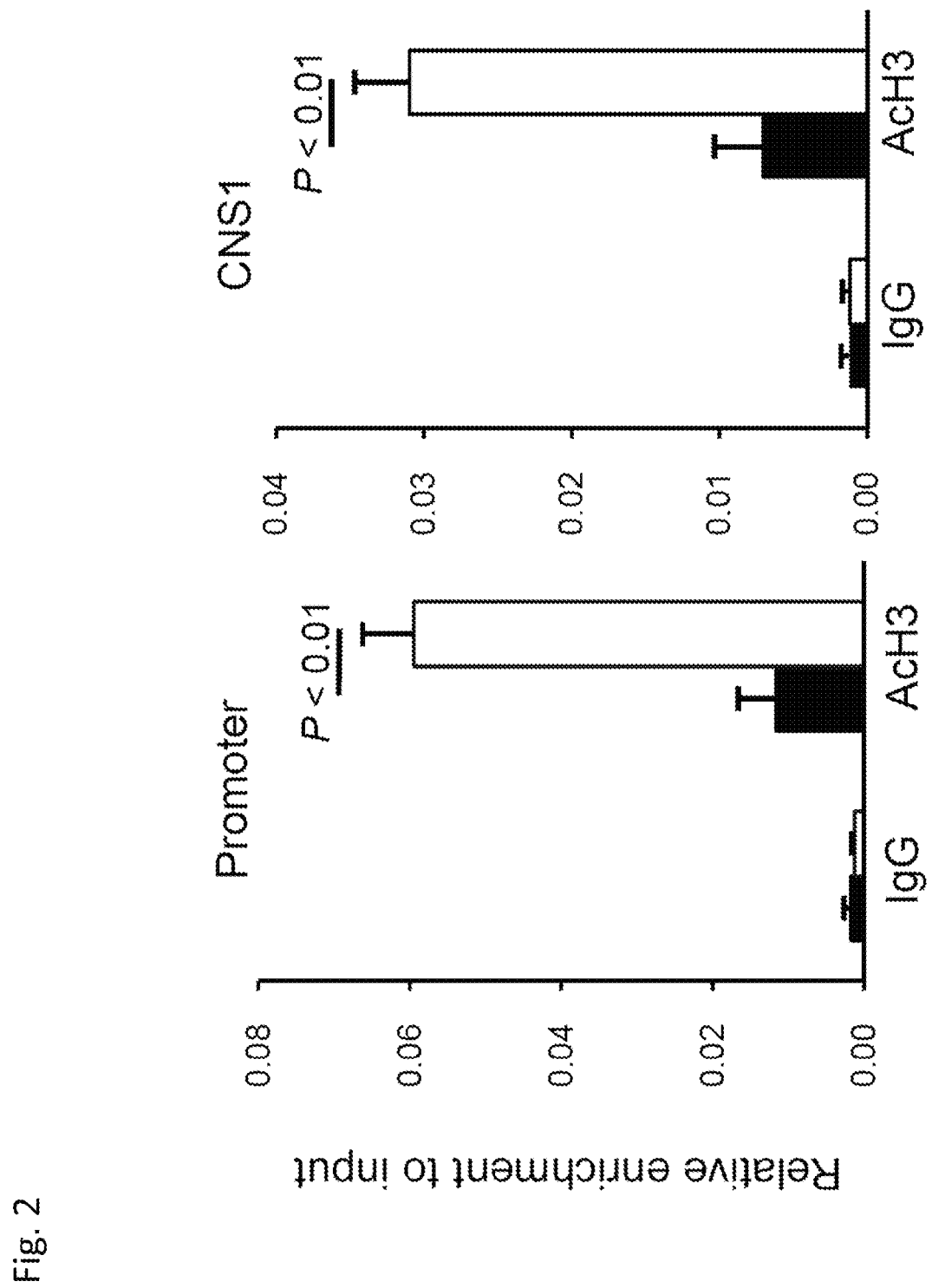
FIG. 2 shows a ChIP-PCR analysis of the Foxp3 promoter and enhancer regions performed in CD4+ T cells cultured with (blank bars) or without (filled bars) butyrate, using anti-acetyl histone H3 antibody (AcH3) or rabbit IgG as a negative reference.

Second, to gain insight into the molecular mechanism of action by which butyrate induces Tregs, assessment was carried out to determine whether butyrate regulates gene expression in T cells. Chromatin immunoprecipitation (ChIP) was performed using MAGnify ChiP system (Invitrogen) according to the manufacturer's protocol. The assay showed that butyrate upregulated histone H3 acetylation in the promoter and conserved non-coding sequence (CNS) 1 in the Foxp3 gene locus (FIG. 2). Other molecules with histone-deacetylase (HDAC) inhibitory properties, such as trichostatin A, (N-(2-aminophenyl)-N'-phenyl-octanediamide), 2-(4-butoxyphenyl)-N-hydroxyacetamide, MS-275, suberoylanilide hydroxamic acid, and RG 2833 similarly can mediate the same effects on Tregs.

Example 3

Figure 3:
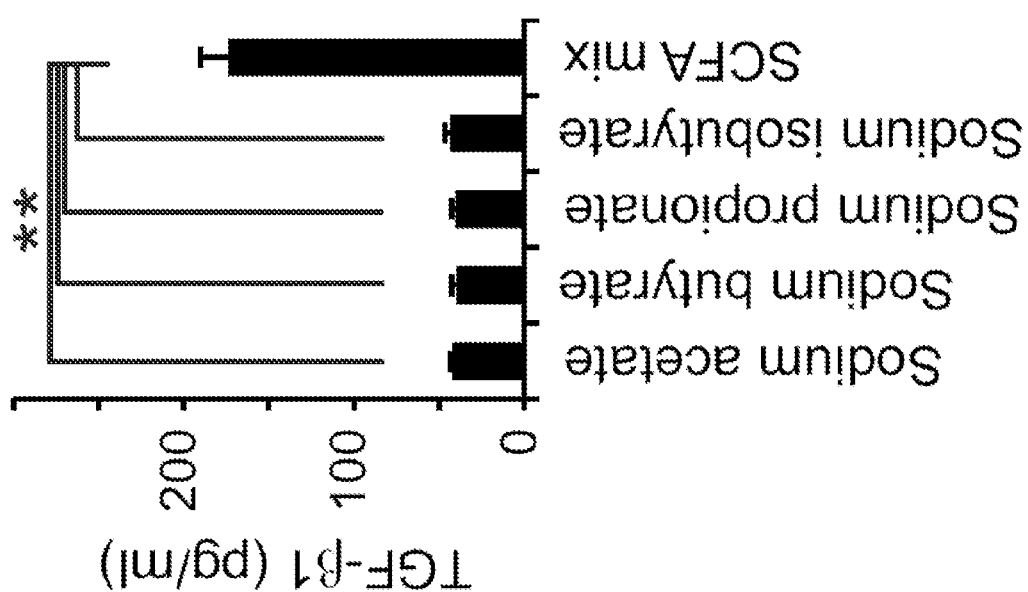
FIG. 3 shows the concentration of active-form TGF-β1 in culture supernatants of epithelial cell line HT29 which has been stimulated either with 0.5 mM sodium acetate, sodium propionate, sodium butyrate, sodium isobutyrate, or their mixture (SCFA mix) for 24h.

Third, each short chain fatty acid identified, as well as a mixture of sodium salts of all the short-chain fatty acids identified, were tested for their ability to induce active form TGF-β1, which is a property representative of the ability of a composition to induce tolerance, increase gut barrier integrity, and reduce inflammation. 0.5 mM solutions of each individual short-chain fatty acid increased expression of active-form TGF-β1 in culture supernatants of epithelial cell line HT29. Surprisingly, a 0.5 mM mixture of sodium salts of acetate, propionate, butyrate, and isobutyrate increased expression of active-form TGF-β1more than three-fold higher than any of the individual short-chain fatty acid solutions alone (FIG. 3). The concentration of active-form TGF-β1 in the culture supernatants was measured by ELISA. These data indicates that the mixture of short-chain fatty acids cooperatively contributes to increased production of active-form TGF-β1.

Example 4

Figure 4:
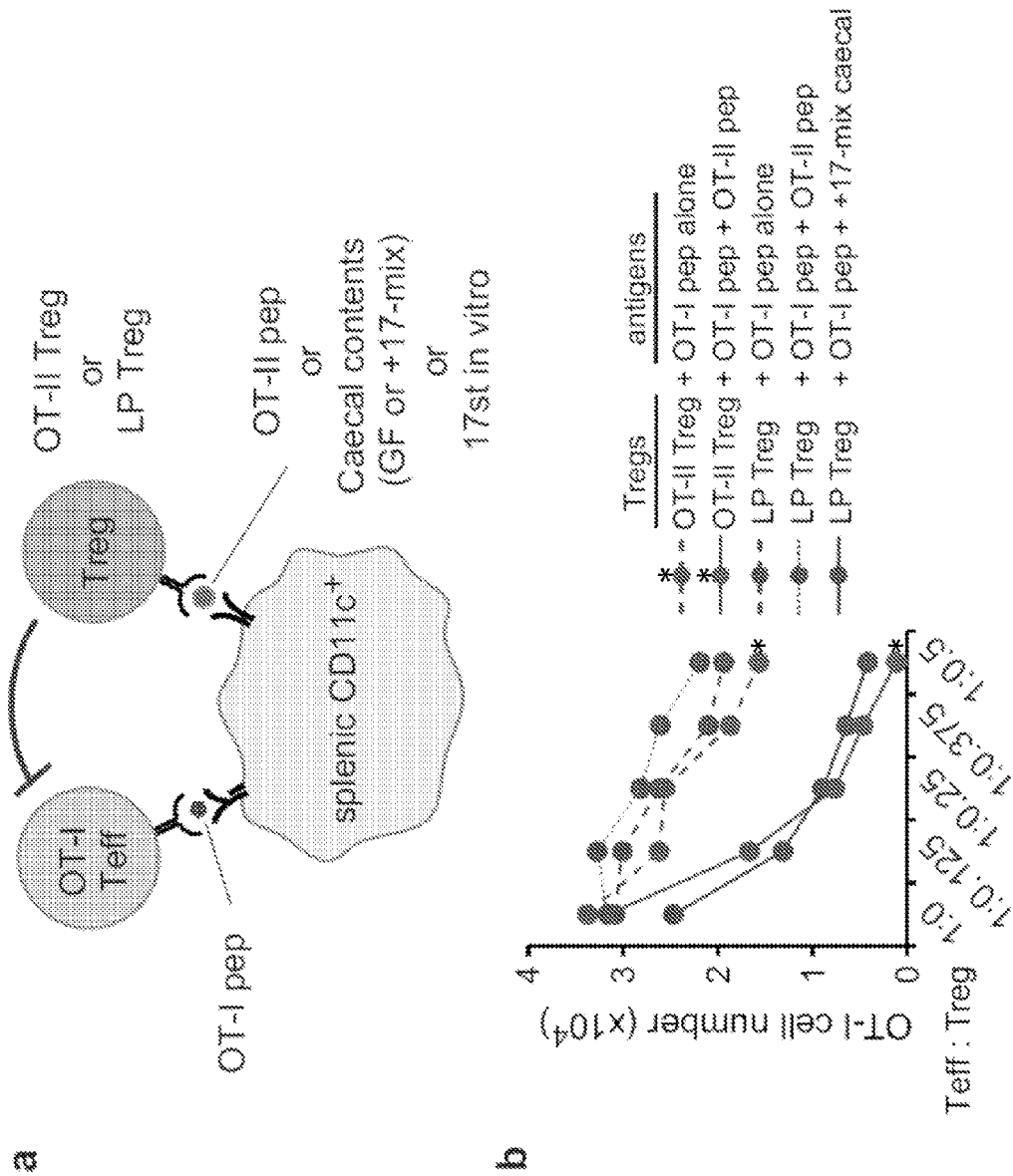
FIG. 4a shows a schematic representation of a cognate antigen-driven suppression assay.
FIG. 4b shows that clostridial antigens are recognized by Treg cells in the lamina propria of gnotobiotic mice colonized with *clostridium* bacteria.
Figure 5:
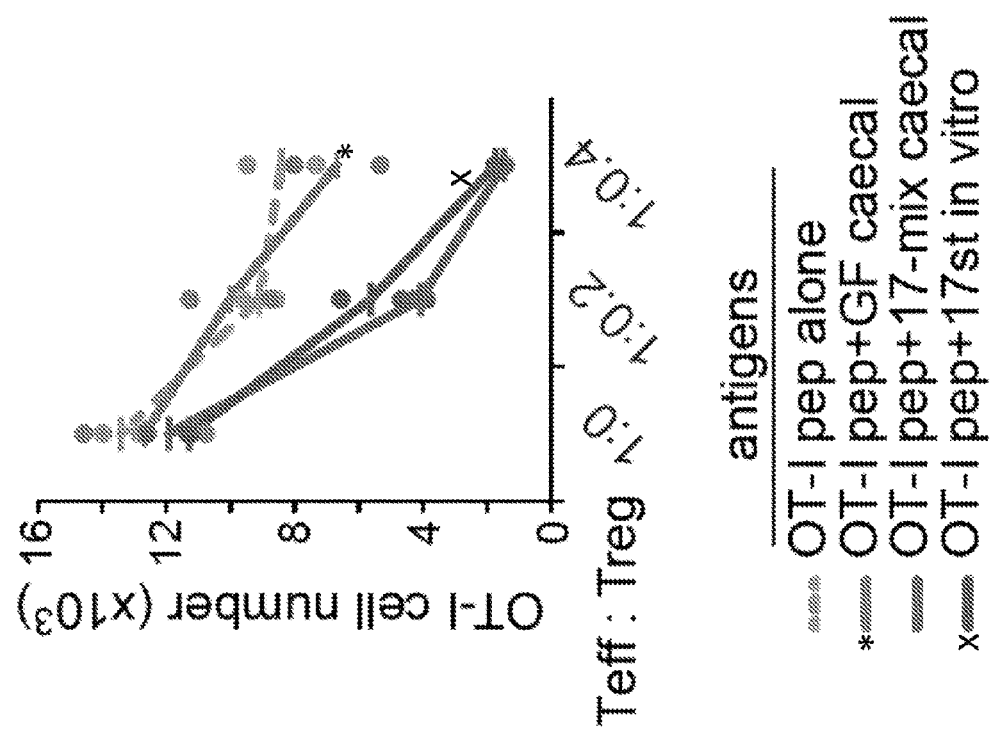
FIG. 5 shows that CD4+CD25+ lamina propria T cells from gnotobiotic mice colonized with a mixture of 17 *Clostridium* strains substantially inhibited the OT-I ovalbumin (OVA) peptide-driven proliferation of OT-I CD8 T cells, and this suppression was markedly enhanced in the presence of autoclaved caecal content from *Clostridium*-colonized mice or autoclaved *Clostridium* strains cultured in vitro, but not in the presence of caecal content from GF mice.

Fourth, investigation was carried to determine whether bacteria belonging to *Clostridium* Clusters IV, XIVa, and XVIII provide bacterial antigens to T cells. To do this, assessment was carried out of the antigen specificity of Tregs accumulated in mice colonized by a mixture of 17 strains belonging to *Clostridium* Clusters, XIVa, and XVIII IV ("17-mix") using a cognate antigen-driven suppression assay. CD4+CD25+ Lamina Propria T cells from mice colonized by 17-mix substantially inhibited the OT-I ovalbumin (OVA) peptide-driven proliferation of OT-I CD8 T cells, and this suppression was markedly enhanced in the presence of autoclaved caecal content from +17-mix mice or autoclaved 17 strains cultured in vitro, but not in the presence of OT-II OVA peptide or caecal content from GF mice (FIGS. 4a-b and FIG. 5). CD11c+cells were isolated from spleens of SPF C57BL/6 mice, pulsed with 0.5 μM SIINFEKL (SEQ ID NO: 2) OT-I peptide alone or in combination with either of 5 μM ISQAVHAAHAEINEAGR (SEQ ID NO: 3) OT-II peptide or autoclaved caecal contents from +17-mix mice, and plated at 5×10$^4$/well. CD8 OT-I T cells (Teff) were added to the CD11c+cell-seeded plates at 5×10$^4$/well. Then, CD4+CD25+ T cells sorted from colonic LP of +17-mix mice (LP Treg) or from spleens of SPF OT-II mice (OT-II Treg) were added to the culture at the indicated ratio of Treg to Teff cells. After 3 days, all cells were harvested, stained with anti-CD4and anti-CD8 antibodies, and analysed by flow cytometry to enumerate the number of CD8 OT-I T cells. Depicted data in FIG. 4b represent average of duplicates. Furthermore, CD8 T cells from OT-I mice (Teff) and the indicated ratio of colon lamina propria CD4+CD25+cells from +17-mix mice (Treg) were incubated with CD11c+ cells pulsed with OT-I peptide alone or in combination with either of autoclaved caecal contents from +17-mix mice (+17-mix caecal) or GF mice (+GF caecal), or autoclaved 17 strains cultured in vitro (+17 st in vitro). Depicted data in FIG. 5 represent average of duplicates. These results demonstrate that some fraction of colonic Lamina Propria Treg cells in *Clostridium*-colonized mice are specific to *Clostridium* bacteria. Collectively, these observations together with the preceding examples, demonstrate that *Clostridium* strains provide short-chain fatty acids and bacterial antigens, which together contribute to differentiation and expansion of colonic Tregs. The same experiment was repeated adding flagellin (SEQ ID NO 1). Flagellin is an antigen highly abundant in bacteria belonging to *Clostridium* Clusters IV, XIVa, and XVIII. Flagellin sequences vary across different microbes. After 3 days, colonic Lamina Propria Treg cells specific for flagellin were isolated.

```
                                        SEQ ID NO: 1
atggtagtac agcacaattt acaggcaatg aactctaaca gaatgttagg catcacacag aagacagcat ctaagtctac agaaaagtta tcttcaggtt acgcaatcaa ccgcgcagca gacaacgcag caggtcttgc tatttctgag aagatgagaa agcagatcag aggacttaca caggcttcta caaatgctga ggacggcatc agctctgtac agacagcaga aggcgctttg acagaagtgc atgatatgct tcagagaatg aacgagctgg caattcaggc agcaaacggc acaaactcag aagatgaccg ctcatacatt caggacgaaa ttgaccagct gacacaggaa atcgatcgtg ttgctgagac aacaaagttc aatgagacat atctcttgaa gggtgacaca aagaacgttg acgctatgga ctatacatat agctataagg cagttacaac gaatactgta gcaagagctt cggttttagc agcagagaac acagctacag gtatgtcagt tagtatttca tttgctgcaa acagcggcaa ggttactgca gctgactcta acaaccttgc aaaggctatc agagatcagg gcttcacaat cacaacatct acccagaatg gtaaggttgt ttacggtctt gagctgaacg gaagcgatgc aaaggcaaac tatacagttt caacagtaag tatggaagct ggtacattca agatcctgaa ttctaataag caggttgttg catctgtaac aatatctaca acagctagct ttaaaaaggt
```

-continued

```
atctggtatg tcacagatcg ttacggcgta ctctgtatca
gcagcttatg cgacgggtga tgtatactct ctctatgacg
cagacggaaa tgcaatttca gcaaacaagc tggataagta
ctttacggca ggcggcgcta cagaggcagg cggaatagct
actacacttt cagcaaactc tggtgtgcct aaggtttatg
acgtactcgg aaaagaggtt tctgcagtaa gcattgcaag
tactttagta acagcagtta aggataagac ggctgcattg
aagatgaact tccatgtagg tgctgacgga acagataaca
acaagattaa gatcaacatt gaggctatga cagctaagag
```

-continued

```
tcttggagtt aacggtctga aggtgagcgg ttcgagcgga
acaaacgcta caaacgctat cgagataatc gctggcgcta
tcaagaaggt ttctacacag agatctgctc ttggtgcggt
tcagaacaga ttagagcaca caatcaacaa cttggataac
atcgttgaga acacaacagc agctgagtca ggaatccgcg
atacagatat ggctacagag atggttaagt actctaacgc
taatatcctt tcacaggcag gtcagtctat gcttgcacag
tctaaccagt ctaaccaggg tgtacttcag ctcttacagt
aa
```

---

What is claimed is:

1. A composition that induces proliferation and/or accumulation of regulatory T cells, the composition comprising:
   (a) one or more short-chain fatty acid or short-chain fatty acid derivative; and
   (b) one or more heat treated inactivated bacteria belonging to *Clostridium* Cluster IV, *Clostridium* Cluster XIVa, or *Clostridium* Cluster XVIII.

2. The composition of claim 1, wherein (a) is selected from the group consisting of butyrate, isobutyrate, propionate, acetate, tributyrin, pivaloyloxymethyl butyrate, and monoacetone glucose 3-butyrate.

3. The composition of claim 1, wherein (a) is butyrate.

4. The composition of claim 1, wherein (a) is a mixture of salts of butyrate, isobutyrate, propionate, and acetate.

5. The composition of claim 1, further comprising a pH sensitive composition comprising an enteric polymer.

6. A pharmaceutical composition comprising the composition according to claim 1 and a pharmaceutically acceptable component.

7. A method for inducing proliferation and/or accumulation of regulatory T cells in an individual in need thereof, the method comprising administering, to the individual, the composition of claim 1.

8. A method of treating, aiding in treating, reducing the severity of, or preventing at least one disease selected from an autoimmune disease, an inflammatory disease, an allergic disease, and an infectious disease in an individual in need thereof, the method comprising administering the composition of claim 1 to the individual.

* * * * *